United States Patent [19]

Weber et al.

[11] Patent Number: 4,703,041

[45] Date of Patent: Oct. 27, 1987

[54] D-GLUCURONIC ACID-UREA CONDENSATE PREPARATION FOR SMOOTHING HUMAN SKIN

[76] Inventors: Gerhard Weber, Lempenmuhle, D-8602, Muhlhausen; Karlheinz Schrader, Max Planck Str. 6, 3450 Holzminden 1, both of Fed. Rep. of Germany

[21] Appl. No.: 772,935

[22] Filed: Sep. 5, 1985

Related U.S. Application Data

[63] Continuation of Ser. No. 543,606, Oct. 20, 1983, abandoned.

[30] Foreign Application Priority Data

Oct. 23, 1982 [DE] Fed. Rep. of Germany ....... 3239317

[51] Int. Cl.$^4$ ........................ A61K 7/48; A61K 31/70
[52] U.S. Cl. ...................................... 514/23; 514/844; 514/845; 514/846; 514/847; 514/937; 514/938
[58] Field of Search ............. 424/DIG. 4, 70; 514/23, 514/844, 845, 846, 847, 937, 938

[56] References Cited

PUBLICATIONS

Chem. Abstracts, 1977–1981, Formula Index $C_7H_{12}N_2O_7$, and Corresponding Citation of Dudkir et al, vol. 88:47065g, 1978.
Pola Chemical Industries, Inc. cited in Chem. Abstracts vol. 94:109088b, 1981.
Niha, cited in Chem. Abstracts vol. 56:6075g, 1962.
CAS Registry Handbook, p. 1774R, No. 4005-18-9.

*Primary Examiner*—Johnnie R. Brown
*Assistant Examiner*—Jacqueline M. Stone
*Attorney, Agent, or Firm*—Bacon and Thomas

[57] ABSTRACT

Skin care preparations and methods are disclosed which contain an effective amount to smooth the skin or reduce scale, of a uronic acid or derivative thereof and particularly a uronic acid urea condensate.

7 Claims, 3 Drawing Figures

D-GLUCURONIC ACID-UREA CONDENSATE PREPARATION FOR SMOOTHING HUMAN SKIN

This application is a continuation of application Ser. No. 543,606, filed Oct. 20, 1983, and now abandoned.

The invention concerns an agent for the care or treatment of human skin.

Many ingredients and compositions are known for smoothing skin. Such compositions often include cellulose based film forming substances. When these substances are used a gel-like surface film is created, which is visible in a disadvantageous manner and is difficult to remove. Furthermore, no natural body substances are used.

The use of salicyclic acid is known for the removal of scale from the skin. However, this leads to the increased formation of callosities, especially on the palm of the hand and the sole of the foot, i.e. it may have a keratoplastic effect which is a disadvantage.

The present invention is intended to provide an improved skin care preparation in relation to the known preparations containing agents for the reduction of roughness of the skin and the elimination of scales, while avoiding the above-mentioned disadvantages.

Accordingly, the present invention comprises a preparation for the care or treatment of human skin comprising a uronic acid or its derivative. The invention also comprises a method for smoothing rough skin which comprises the application of a uronic acid containing composition to the skin for the reduction of skin roughness. Better smoothing of the skin than with the known film formers is obtained, while the preparation applied is not visible, as no film is formed. A uronic acid is a natural product of the body and when in the skin is therefore especially compatible with the skin. It may be combined with other natural body substances.

The invention has as an object the application of a uronic acid for the removal of scales from the skin. Here again, the aforementioned advantage of the use of a natural product persists. The disadvantageous keratoplastic effect of salicyclic acid is therefore avoided.

The uronic acid may be a hyaluronic acid, an iduronic acid or in a preferred embodiment, a glucuronic acid. In the last case a D-glucuronic acid is especially preferred, which is readily synthesized. Hyaluronic acid, iduronic acid and glucuronic acids are all natural body substances.

In a particularly advantageous form of the invention, a condensate of a uronic acid and urea is the active ingredient in the aforementioned preparations and may be present in an amount of from 1 to 9%, optimally 5% by weight of the total preparation. A preferred condensate comprises the condensation product of D-glucuronic and urea. This condensate has the formula $C_7H_{12}O_7N_2 = HO_2C.[CH(OH)]_4.CH:N.Co.NH_2$ or its isomeric forms. The structural formula of this condensation product is as follows:

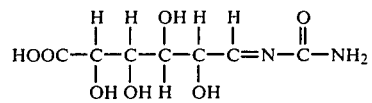

D-glucuronic acid is found in the aldehyde, pyranose or furanose form. It is present among other metabolites in the body and they are participates in detoxification processes in the liver. It has now been discovered by means of roughness measurements according to Padberg (J. SOC. Cosmetic Chemists 20, 719–728, 1969) that glucuronic acid in a water/oil emulsion improves the smoothness of skin by approximately 6.5% with respect to the placebo values.

In view of the low pH value of this acid (approximately 1.8 in a 10% aqueous solution) it appeared obvious to prepare the sodium salt by the reaction of glucuronic acid with sodium hydroxide in a stoichiometric ratio. This compound had a pH value of 7.1 but yielded, when used in the same emulsion and concentration (5%) an improvement of roughness of only approximately 0.5%.

The results obtained with glucuronic acid were satisfactory, while use of the sodium salt was not. The use of a D-glucuronic acid with a sodium salt was thus rejected.

The condensation product of urea and D-glucuronic acid decomposes upon concentration of the aqueous solution or boiling with alkalies or dilute mineral acids into urea and D-glucuronic acid. It is highly soluble in water and insoluble in organic solvents.

Testing of human skin with the aforementioned water/oil emulsion shows an improvement with respect to the placebo (designated by "P1") of 11%. This test was effected on 10 subjects between 11 and 65 years in age. In a parallel series, in further sample emulsions of the oil/water type, the same serial experiment was repeated using the aforementioned substances in the same concentration, in comparison with distilled water (designated "W"). It was discovered in the process that with respect to the initial clear value of the skin (designated by "H"), the improvement was greatest with the use of the glucuronic acid-urea condensate, followed by the formulation employing pure glucuronic acid and the use of the sodium salt of glucuronic acid. The placebo value was the poorest here again.

Table I tabulates the sample formulations, with the supplemental indication whether a water/oil (W/O) emulsion or an oil/water (O/W) emulsion is involved. (In cosmetics, oil/water emulsions are preferably used in a product to be applied during the day and water/oil emulsions in products to be applied at night).

TABLE I

| Raw materials: | 271/25 W/O % | 271/26 W/O % | 271/27 W/O % | 271/28 O/W % | 271/29 O/W % | 271/30 O/W % | 271/31 W/O % | 271/32 O/W % |
|---|---|---|---|---|---|---|---|---|
| Sorbitanmonooleate | 3 | 3 | 3 | | | | 3 | |
| Isopropylstearate | 5 | 5 | 5 | 6 | 6 | 6 | 5 | 6 |
| Paraffin oil, beads | 15 | 15 | 15 | 5.5 | 5.5 | 5.5 | 15 | 5.5 |
| Preservative | 0.2 | 0.2 | 0.2 | 0.2 | 0.2 | 0.2 | 0.2 | 0.2 |
| Condensation product of propylene oxide and ethylene oxide | 3 | 3 | 3 | | | | 3 | |
| Synthetic wax of long | 5 | 5 | 5 | | | | 5 | |

TABLE I-continued

| Raw materials: | 271/25 W/O % | 271/26 W/O % | 271/27 W/O % | 271/28 O/W % | 271/29 O/W % | 271/30 O/W % | 271/31 W/O % | 271/32 O/W % |
|---|---|---|---|---|---|---|---|---|
| chain fatty acids and fatty alcohols | | | | | | | | |
| Glycerinmonostearate | | | | 6 | 6 | 6 | | 6 |
| Lanolin alcohol | | | | 2 | 2 | 2 | | 2 |
| Stearic acid | | | | 2.5 | 2.5 | 2.5 | | 2.5 |
| Cetyl alcohol | | | | 1 | 1 | 1 | | 1 |
| Spermaceti | | | | 1.5 | 1.5 | 1.5 | | 1.5 |
| 2-ethylhexylpalmitate | | | | 3 | 3 | 3 | | 3 |
| Vaseline | | | | 4 | 4 | 4 | | 4 |
| Silicone oil | | | | 1 | 1 | 1 | | 1 |
| Condensation product of urea and D-glucuronic acid 50% in $H_2O$ | 10 | | | 10 | | | | |
| D-glucuronic acid | | 5 | | | 5 | | | |
| Sodium salt of D-glucuronic acid | | | 5 | | | 5 | | |
| Sorbitol | 5 | 5 | 5 | 5 | 5 | 5 | 5 | 5 |
| $H_2O$ | 53.8 | 58.8 | 58.8 | 51.65 | 56.65 | 56.65 | 63.8 | 61.65 |
| Imidazolidinyl-urea compound containing methylol groups | | | | 0.45 | 0.45 | 0.45 | | 0.45 |
| Hydroxyethyl cellulose | | | | 0.2 | 0.2 | 0.2 | | 0.2 |

The drawings depict graphically experimental results in which

Figure 1:
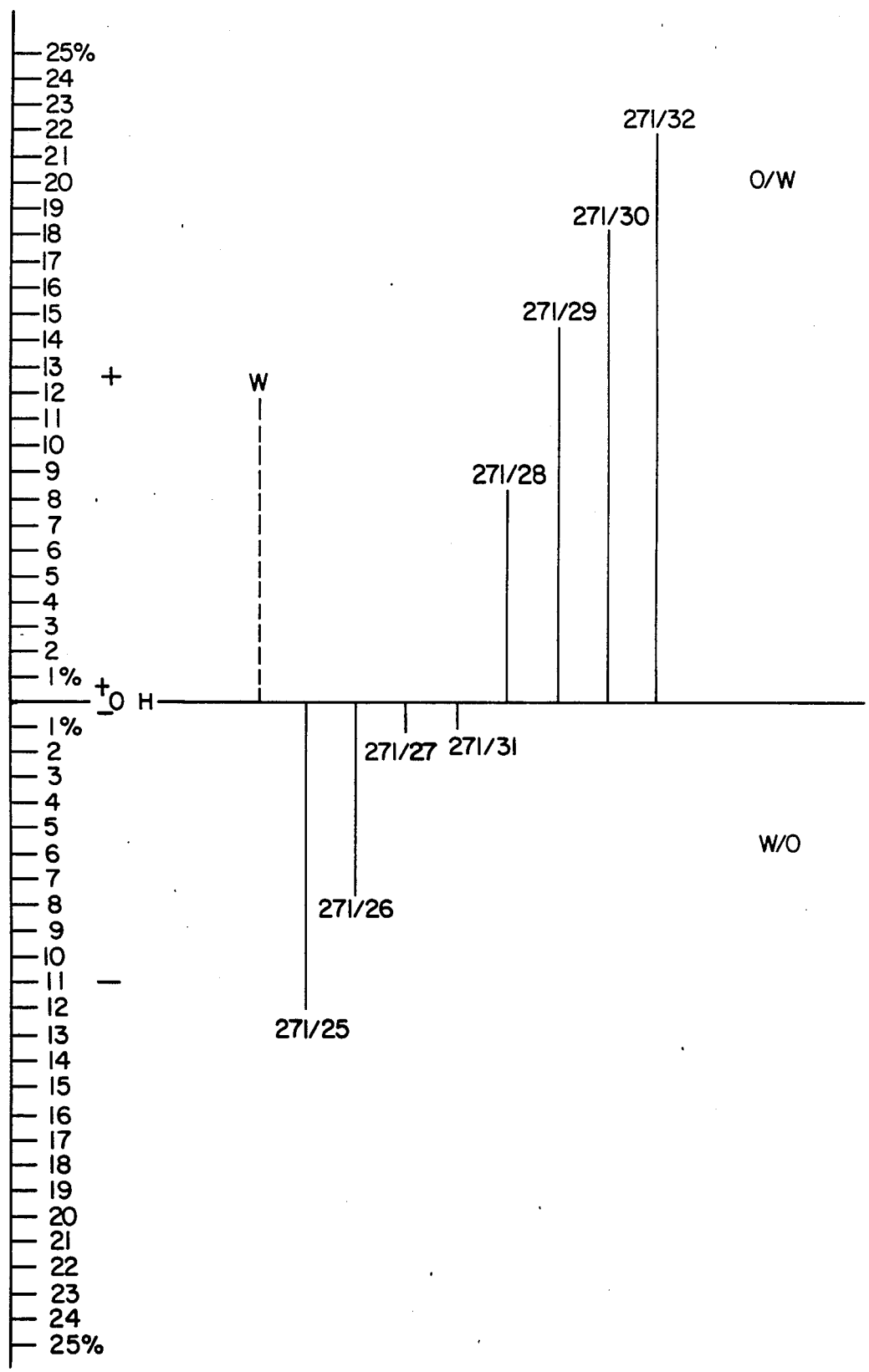
FIG. 1 shows the roughness of skin.

FIG. 1 shows graphically the roughness of skin obtained in the individual experiments according to Table I with the aforecited 10 subjects 10 to 65 years of age. The numbers of the formulations in Table I are indicated. Roughness increases on the ordinate from bottom to top. The values given should be multiplied by 0.5 as a 50% aqueous solution of the concentrate in water is used. Below the abcissa the experiments are in a water-/oil emulsion and above the abcissa the experiments are in an oil/water emulsion. It is seen that the roughness is least with a water/oil emulsion. It is further seen that Experiments No. 25 and 28 give the best results respectively within their water/oil or oil/water systems, i.e. they result in the least roughness within their system. In Experiments 25 and 28 the proportion of the condensation product of uea and D-glucuronic acid, 50% in $H_2O = 10$, i.e. with respect to the total volume equals 5%.

Experiments No. 26 and 29 involve the use of a D-glucuronic acid, but without condensation with urea. Even though they yield usable values, these are not the optimum values of Experiments 25 and 28 with a condensation product of urea and D-glucuronic acid.

Figure 2:
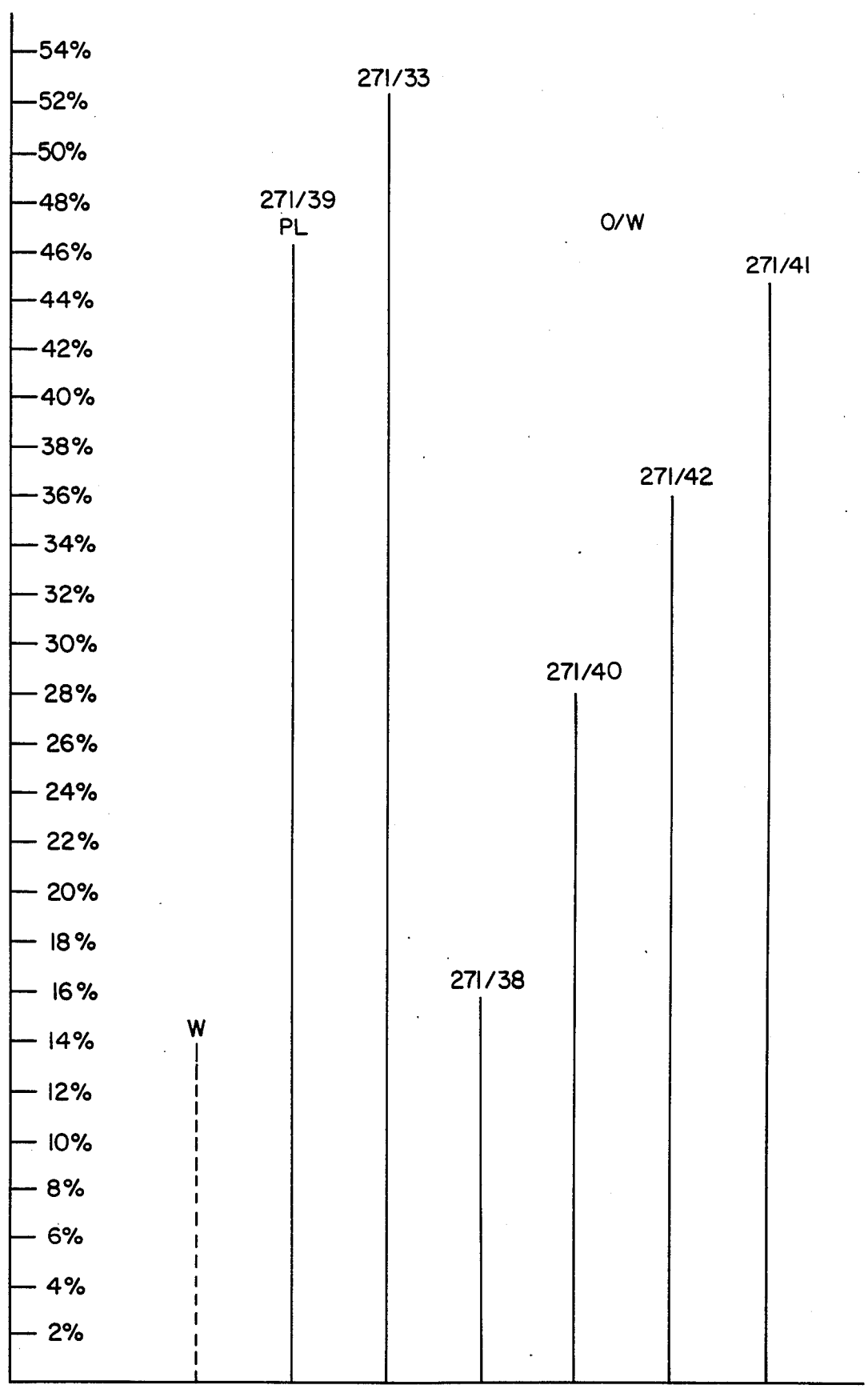
FIGS. 2 and 3 show results for a condensate at constant pH.
Figure 3:
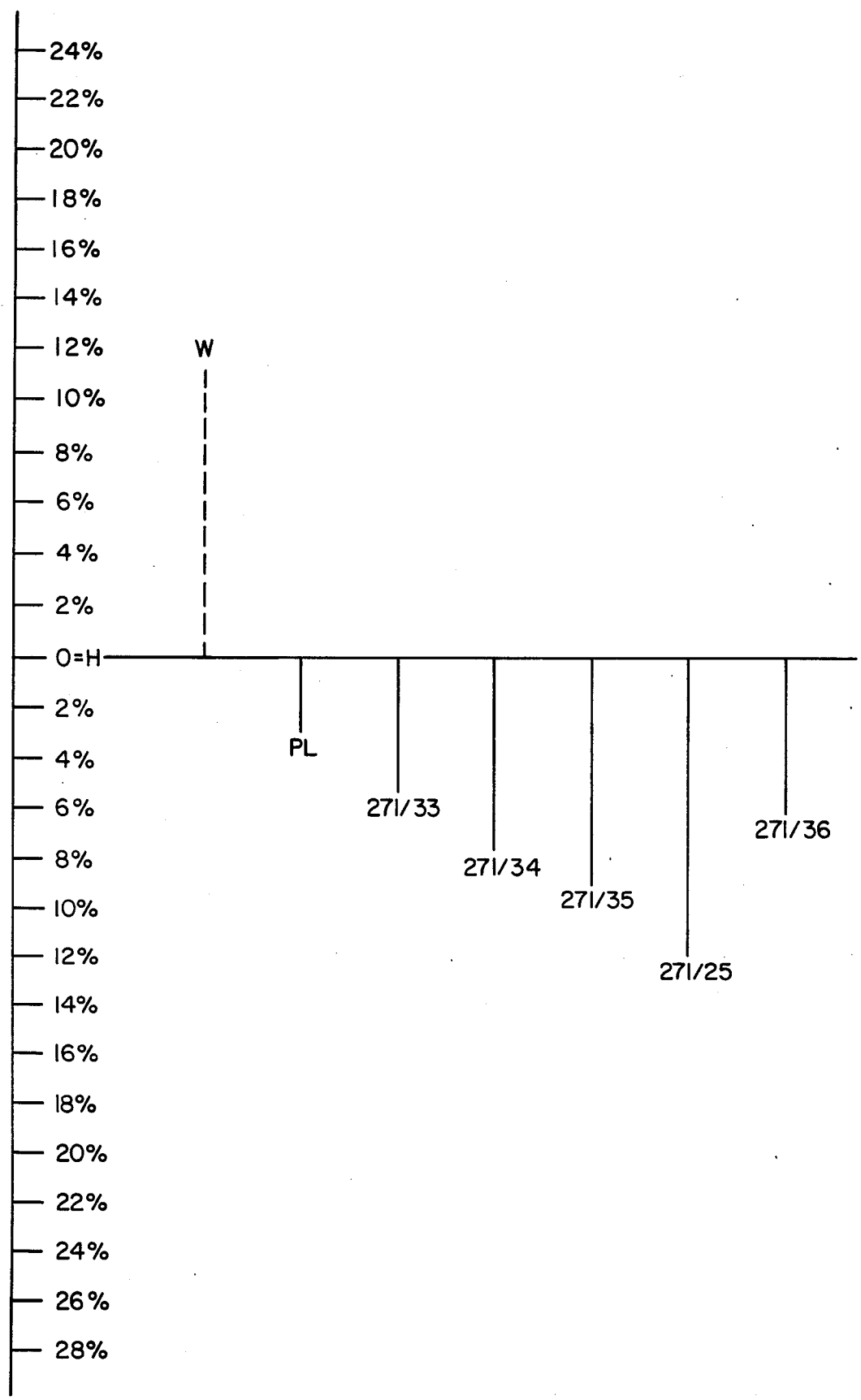

FIGS. 2 and 3 record the results of experiments performed to determine, at a constant pH value of 6, the best concentration of the condensation product of urea and D-glucuronic acid in sample emulsions of the oil/water type, (FIG. 2) and water/oil type (FIG. 3). Here again, roughness increases, given in %, on the ordinate from bottom to top. Values must be again multiplied by 0.5.

In FIG. 2, concentration optimizations at pH 6 in an oil/water emulsion are presented as follows:

| | |
|---|---|
| W = water | +14.0% roughness |
| P1 = placebo | +46.2% roughness |
| 271/37 = 10% glucuronic acid condensate | +52.0% roughness |
| 271/38 = 5% glucuronic acid condensate | +15.8% roughness |
| 271/40 = 3% glucuronic acid condensate | +28.0% roughness |
| 271/42 = 2% glucuronic acid condensate | +36.0% roughness |
| 271/41 = 1% glucuronic acid condensate | +44.8% roughness | with 5 subjects 42 to 64 years of age.

FIG. 3 shows analogous experiments with 5 subjects 42 to 71 years of age in a water/oil emulsion at a pH value of 6, resulting in the following values:

| | |
|---|---|
| W = water | +11.2% roughness |
| P1 = placebo | −3.0% roughness |
| 271/33 = 1% glucuronic acid condensate | −4.7% roughness |
| 271/34 = 2% glucuronic acid condensate | −7.5% roughness |
| 271/34 = 3% glucuronic acid condensate | −9.0% roughness |
| 271/25 = 5% glucuronic acid condensate | −12.0% roughness |
| 271/36 − 10% glucuronic acid condensate | −5.4% roughness |

In both cases the best smoothing action was obtained with a 5% concentration of the urea condensate. Any increase (or reduction) of this proportion leads always to a deterioration of skin smoothness. The upper limit was at approximately 9% and the lower at 1% concentration.

Uronic acid, especially its condensation product with urea, may be included as a skin smoothing agent in other compositions which may contain other active ingredients. Such compositions include bathing preparations, showering preparations and dish washing liquids with skin care agents, in the dissolved state. The preparations of the present invention may contain conventional carrier substances, diluents and auxiliary substances. The following preparations exemplify the invention. In the preparations, the raw materials are listed along with their weight percentages based on the weight of the composition. The preparations are worked into the formation of an emulsion.

| Raw materials: | % |
|---|---|
| PREPARATION A | |

| Raw materials: | % |
|---|---|
| Sorbitanmonooleate | 3 |
| Paraffin oil, beads | 20 |
| Preservative | 0.2 |
| Condensation product of propylene oxide and ethylene oxide | 3 |
| Synthetic wax of long chain fatty acids and fatty alcohols | 5 |
| D-glucuronic acid | 5 |
| H₂O ad | 100 |
| PREPARATION B | |
| Paraffin oil, beads | 15.5 |
| Preservative | 0.2 |
| Glycerinmonostearate | 2.5 |
| Cetyl alcohol | 1 |
| Spermaceti | 1.5 |
| 2-ethylhexylpalmitate | 3 |
| Vaseline | 4 |
| D-glucuronic acid | 5 |
| H₂O ad | 100 |
| PREPARATION C | |
| Sorbitanmonooleate | 3 |
| Paraffin oil, beads | 20 |
| Preservative | 0.2 |
| Condensation product of propylene oxide and ethylene oxide | 3 |
| Synthetic wax of long chain fatty acids and fatty alcohols | 5 |
| Condensation product of urea and D-glucuronic acid, 50% in H₂O | 10 |
| H₂O ad | 10 |
| PREPARATION D | |
| Paraffin oil, beads | 15.5 |
| Preservative | 0.2 |
| Glycerinmonostearate | 6 |
| Stearic acid | 2.5 |
| Cetyl alcohol | 1 |
| Spermaceti | 1.5 |
| 2-ethylhexylpalmitate | 3 |
| Vaseline | 4 |
| Condensation product of urea and S-glucuronic acid, 50% in H₂O | 10 |
| H₂O ad | 100 |
| Imidazolidinyl-urea compound containing methylo groups | 0.45 |

We claim:

1. A composition for smoothing human skin which comprises a skin smoothing effective amount of D-glucuronic acid-urea condensate in a water/oil or oil/water emulsion; said condensate having the formula:

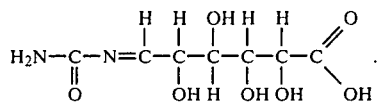

2. The composition of claim 1 wherein the D-glucuronic acid-urea condensate is present in an amount of 1-9% by weight with respect to the entire composition.

3. The composition of claim 2 wherein the D-glucuronic acid-urea condensate is present in an amount of 5% by weight with respect to the entire composition.

4. A method for smoothing human skin which comprises applying thereto a composition which comprises a skin smoothing effective amount of D-glucuronic acid-urea condensate in a water/oil or oil/water emulsion; said condensate having the formula:

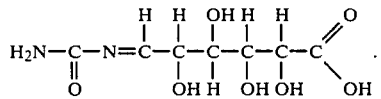

5. The method of claim 4 wherein the composition contains D-glucuronic acid-urea condensate in an amount of 1-9% by weight with respect to the entire composition.

6. The method of claim 5 wherein the composition contains D-glucuronic acid-urea condensate in an amount of 5% by weight with respect to the entire composition.

7. A method for smoothing human skin which comprises applying thereto a composition containing a skin smoothing effective amount of D-glucuronic acid-urea condensate having the formula:

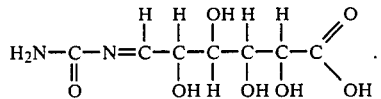

* * * * *